United States Patent [19]
Eicher et al.

[11] Patent Number: 6,132,755
[45] Date of Patent: *Oct. 17, 2000

[54] TRANSCORNEAL DRUG-RELEASE SYSTEM

[75] Inventors: Joachim Eicher, Dortmund; Bernd Zierenberg, Bingen/Rhein, both of Germany

[73] Assignee: Boehringer Ingelheim KG, Ingelheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/983,197
[22] PCT Filed: Jul. 15, 1996
[86] PCT No.: PCT/EP96/03090
§ 371 Date: Jun. 16, 1998
§ 102(e) Date: Jun. 16, 1998
[87] PCT Pub. No.: WO97/03718
PCT Pub. Date: Feb. 6, 1997

[30] Foreign Application Priority Data

Jul. 14, 1995 [DE] Germany .......................... 195 25 607

[51] Int. Cl.[7] .............................................. A61F 2/14
[52] U.S. Cl. .............................................. 424/427
[58] Field of Search ............................... 424/427

[56] References Cited

U.S. PATENT DOCUMENTS

3,964,482  6/1976  Gerstel et al. ............................ 128/260

Primary Examiner—Carlos A. Azpuru
Attorney, Agent, or Firm—R. P. Raymond; A. R. Stempel; M-E M. Devlin

[57] ABSTRACT

The invention refers to a transcorneal system for the actively controlled transcorneal delivery of a medicament into a subject comprising an active substance reservoir and a device provided with a plurality of micro-pins or micro-blades adapted in use to penetrate the stratum corneum of the subject and connected with reservoir via a liquid conveying connection and thereby allow active substance to pass from the reservoir through capillary openings of the micro-pins or along the micro-blades into the subject.

21 Claims, 6 Drawing Sheets

TRANSCORNEAL DRUG-RELEASE SYSTEM

This application is a 371 continuation of PCT/EP96/03090, filed Jul. 15, 1996.

The present invention relates to a new drug release system for the controlled release of drugs over a long period of time.

According to the invention, a transcorneal system for the controlled supply of drugs avoiding the gastrointestinal tract is claimed, which consists essentially of a device which makes it possible to administer a medicinal composition over a long period of time whilst avoiding the corneal skin layers.

The apparatus according to the invention consists essentially of a reservoir for the drug and at least one—typically several—micro-pins provided with capillary openings which are connected to the reservoir in such a way that the drug in the form of a solution containing the active substance passes from the reservoir into the micro-pins. When the transcorneal system is placed on the skin, the Stratum corneum and possibly the epidermis are penetrated by the micro-pins so as to provide direct access to the innervated layer of the skin. In this way the drug can pass from the reservoir through the capillary openings of the micro-pins into vascularised sections of the skin from where it is absorbed into the bloodstream through the capillary circulatory system. Instead of the micro-pins, micro-blades may be used, which scratch the skin when the system is applied.

An essential advantage of the system according to the invention is that the skin barrier for transdermally administered drugs, namely the Stratum corneum, is circumvented with the system according to the invention.

It is precisely the individually different properties of the uppermost horny layer in patients which are the reason for problems such as insufficient bioavailability and allergies when active substances are administered transdermally. One particular advantage of transcorneal administration is that this method of administration is not restricted to those active substances which penetrate through the skin, as is the case with transdermal administration, for example. Examples of suitable active substances include pain killers such as morphine, naltrexone, fentanyl, oxymorphone; anti-Parkinson's agents such as L-dopa, pramipexole; heart and circulatory drugs, nitroglycerin, drugs to combat high blood pressure and vasodilatory disorders, such as clonidine, nifidepine, verapamil and diltiazam; anticoagulants such as heparin and hirudin; agents for long-term therapy in cancers and immune diseases; agents for the long-term treatment of addiction; peptides; ACE-inhibitors; neurokinin antagonists; and hormones such as oestradiol.

Usually, the active substance is present in the form of a solution to allow satisfactory travel through the capillary openings of the micro-pins of the transcorneal system. Theoretically, all physiologically acceptable solvents or solvent mixtures in which the active substance is soluble in a sufficient quantity may be used. The phrase "sufficient quantity" is taken to mean those concentrations of active substance in the solvent which make it possible to administer a therapeutically effective quantity of active substance.

The preferred solvents are water and ethanol. If it should be necessary, solubilisers and complexing agents may be used to increase the solubility of the active substance in the solvent. Delicate active substances may be mixed with additives to increase their shelf life.

The system according to the invention contains a reservoir for storing the active substance solution, whilst a liquid-conveying connection between the reservoir and the micro-pins makes it possible for the drug to be conveyed from the reservoir through the capillary openings of the micro-pins and below the Stratum corneum, so that the drug can be introduced directly into the bloodstream whilst avoiding the outer horny layers.

The transportation of the drug—e.g. in the form of an aqueous solution—may be either "passive", i.e. achieved by the existing concentration gradient between the concentration of the active substance solution in the reservoir and in the blood, or "active", e.g. by means of an overpressure stored in the reservoir, electrostatic or capillary forces, or a pump integrated in the system. Preferably, the solution of active substance is transported actively, e.g. by means of a pump or a piezoelectric membrane. The flow volume (ml/time) of the drug may be adjusted or monitored by means of one or more additional valves or a constriction between the reservoir and the micro-pins.

Depending on the size of the reservoir, the concentration of active substance and the therapeutic dose needed, the transcorneal system according to the invention is suitable for a period of administration of one or more days up to 4 weeks or longer, preferably 7 to 14 days.

In one embodiment, the system is so miniaturised in terms of its dimensions and weight, that it can readily be carried on the skin or fixed in the skin, like a plaster or a wristwatch, for a lengthy period. The transcorneal system may be secured by means of an armband, an adhesive tolerated by the skin or by the micro-pins themselves.

The manufacture of the system according to the invention and the filling of the reservoir are carried out under controlled conditions—for reasons of drug safety, the system according to the invention may be sealed or packed in airtight manner under sterile conditions until ready for use.

Usually, the reservoir and micro-pins of the system according to the invention form a one-part or multi-part constructional unit in a housing. However, embodiments are conceivable in which the reservoir and micro-pins are structurally separate from one another and joined together by a thin tube or capillary. This is particularly advantageous when large quantities of drug are to be administered over a lengthy period.

The technical and constructional design of the micropins and the capillary openings which serve to deliver the solution of active substance are of crucial importance to the functioning of the transcorneal system according to the invention.

In order to penetrate the *Stratum corneum*, the micropins must have a length of at least 10 µm, preferably 50 to 100 µm more preferably up to 1 mm. The micro-pins according to the invention extend conically or cylindrically, the rounding radii of the tips of the pins typically being in the micron range, preferably smaller than 10 µm. This minimises the injury to the skin and the sensation of pain during administration. In order to ensure an adequate delivery of the solution of active substance into the capillary circulation of the patient, the micro-pins according to the invention have capillary openings, e.g. in the form of bores or slots or a combination of both. Micro-pins consisting of a material having a defined porosity also enable the solution of active substance to be delivered.

Particular embodiments of the micro-pins according to the invention may, for example, have capillary openings in the form of a combination of a central bore with outward slots.

The transporting of the solution of active substance may be aided or regulated, depending on the viscosity of the solution, by mechanical, electrical, chemical and/or surfactant forces. For reasons of redundancy—but also in order to adjust the flow volume and the line resistance—it is preferable to use a plurality of micro-pins for each transcorneal system. Usually, the micro-pins are arranged on a surface which forms the side of the transcorneal system facing the skin. This surface may be between a few square millimeters and a few square centimeters. A typical number of micro-pins is between 10 and 100, although this number should not restrict the inventive concept in any way.

The active substance from which the micro-pins are produced must be tolerated by the skin and be biocompatible. In the interests of cheap mass production, as well as ceramic materials, glasses and metals such as titanium are suitable. Easily workable plastics are preferred. Biodegradable polymers such as polylactides and the like have the advantage that any particles of the pins remaining in the skin can be broken down. Biodegradable polymers have long been known in the art and have proved useful, for example, as suturing material and bone pins.

Figure 1:
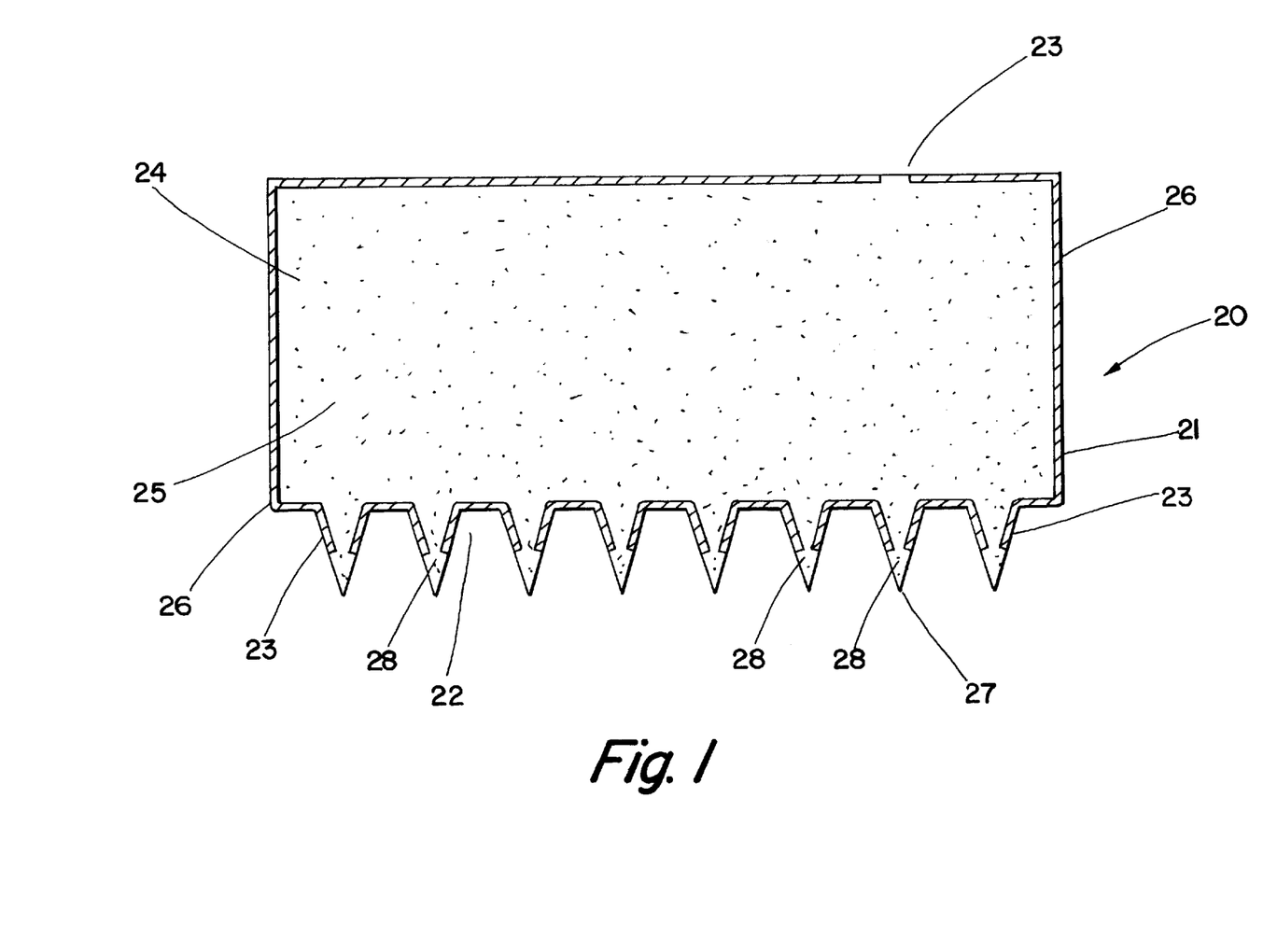
FIG. 1 shows a cross-sectional view of a transcorneal therapeutic system.

FIG. 1 shows a particularly simple embodiment of the transcorneal system (20) in axial section. The system consists of a container (21) with micro-pins (23) formed on the base (22). The interior of the container acts as a reservoir (24) for receiving the solution of active substance (25). Depending on the viscosity, the solution of active substance is present as such directly in the reservoir or is stored in a matrix, e.g. of an absorbent material or a polymer.

The container and micro-pins have a fluidtight outer wall (26) which is mechanically strong enough to ensure that the system for activating the drug release can be placed on the skin and the micro-pins can be pressed into the skin using light pressure. Since the outer wall (26) is pierced in the region of the tips (27) of the micro-pins and forms an outlet opening (28), the solution of active substance is able to enter the capillary circulatory system by capillary force, thereby circumventing the transcorneal layer of skin, and from there it develops its systemic activity. In the region of the reservoir there may be a device (29) for providing a pressure equalising ventilation. Usually, the ventilation device is provided with a filter to ensure that no impurities can enter the system. In order to aid the flow of active substance solution, a device may be provided to exert additional pressure on the reservoir. The system is filled, for example, by injecting the solution of active substance into the reservoir, by immersing the system in a solution of active substance or by placing a matrix impregnated with the active substance in the system.

It is obvious that in the latter case the transcorneal system is of two-part construction, e.g. it comprises a lower part which forms the micro-pins and an upper part with which the system is closed off once the active substance matrix has been put in. Depending on the type of active substance, this may be present in dissolved form in an aqueous or organic physiologically acceptable solvent or mixture of solvents. Examples of suitable solvents include water, ethanol, propanol and mixtures thereof. However, the active substances may also be dissolved in a matrix consisting of a gel, e.g. a polymeric material.

Materials which may be used to produce the container and the micro-pins include primarily thermoplastic materials which may be sintered in a mould starting from fine granules. By a suitable choice of the parameters of pressure, temperature (typically and below the melting temperature of the material) and time, a reproducible porosity (typically 50%) is achieved. By subsequently melting the surface of the component in a controlled manner it is sealed so as to produce a porous container with a leaktight outer wall. Areas of the wall which should be kept permeable, such as the ventilation devices and the tips of the pins, are kept below the melting temperature by cooling. In order to seal off the porous wall, it is also possible to use coatings and sealants, but these are technically more complex. The degree of porosity and the cross-sections of release at the tips of the pins are variable within wide limits and thus constitute parameters for adjusting the metering rate. Examples of other suitable materials include polyethylenes, polypropylenes or polysulphones.

Figure 2:
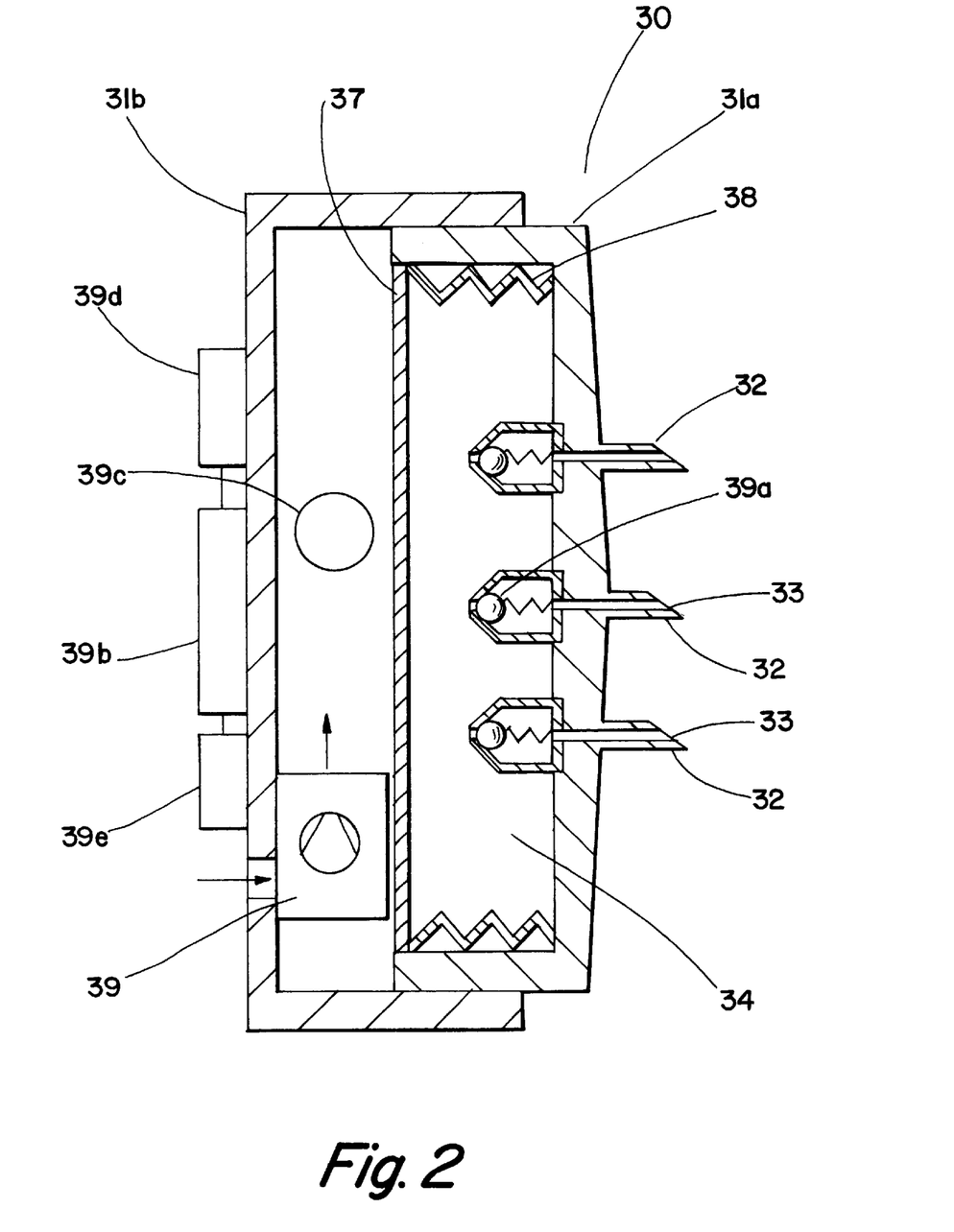
FIG. 2 shows a cross-sectional view of a transcorneal therapeutic system employing micro-valves to control the fluid rate of the drug-containing fluid.

A further developed system is shown in FIG. 2. The transcorneal system (30) consists of a lower housing part (31a) and an upper housing part (31b). The lower housing part (31a) contains, on the side facing the surface of the skin, micro-pins (32) with the capillary openings (33), only three of which are shown in the drawings, albeit on a larger scale in the interests of clarity. The reservoir (34) for the solution of active substance is formed by a movable plunger (37) and at the sides of the lower part of the housing by a concertina seal (38). The concertina seal may, naturally, be replaced by other sealing provisions, e.g. by precision guiding of the plunger in the lower part of the housing. The upper housing part contains the micropump (39) which exerts a defined pressure on the plunger and thereby administers the active substance through the micro-pins into the capillary circulatory system. On the inside of the lower housing part, microvalves (39a) may be provided in front of the capillary openings to prevent premature release of the drug. The pressure on the plunger may be exerted pneumatically by the pump, but in another embodiment it may be provided by means of a miniaturised electric motor and a transmission connected thereto, by a purely mechanical method.

In order to improve the controllability and adjustability of the metering of active substance, the system may be extended to include microsensors (39c), microactuators (39e), e.g. for actively controlling the microvalves (not shown), an electronic circuit (39b) with input/output possibilities (39d) and a current supply. The sensors serve primarily to detect and monitor controlled variables and disturbance variables, such as, for example, the concentration of active substance in the blood, the temperature or activity level of the patient, and to detect and monitor system variables such as time, throughflow, pressure and temperature. The memory area of the electronic circuit can be programmed with nominal data and parameters by the manufacturer or by the doctor or patient using a suitable interface. The measurements picked up by the sensors are detected by the electronics and further processed. The control signals for the microactuators are derived therefrom depending on the given control and regulating function.

An essential component of the transcorneal system according to the invention is the construction of the micro-pins.

Figures 3A, 3B, 3C, 3D:
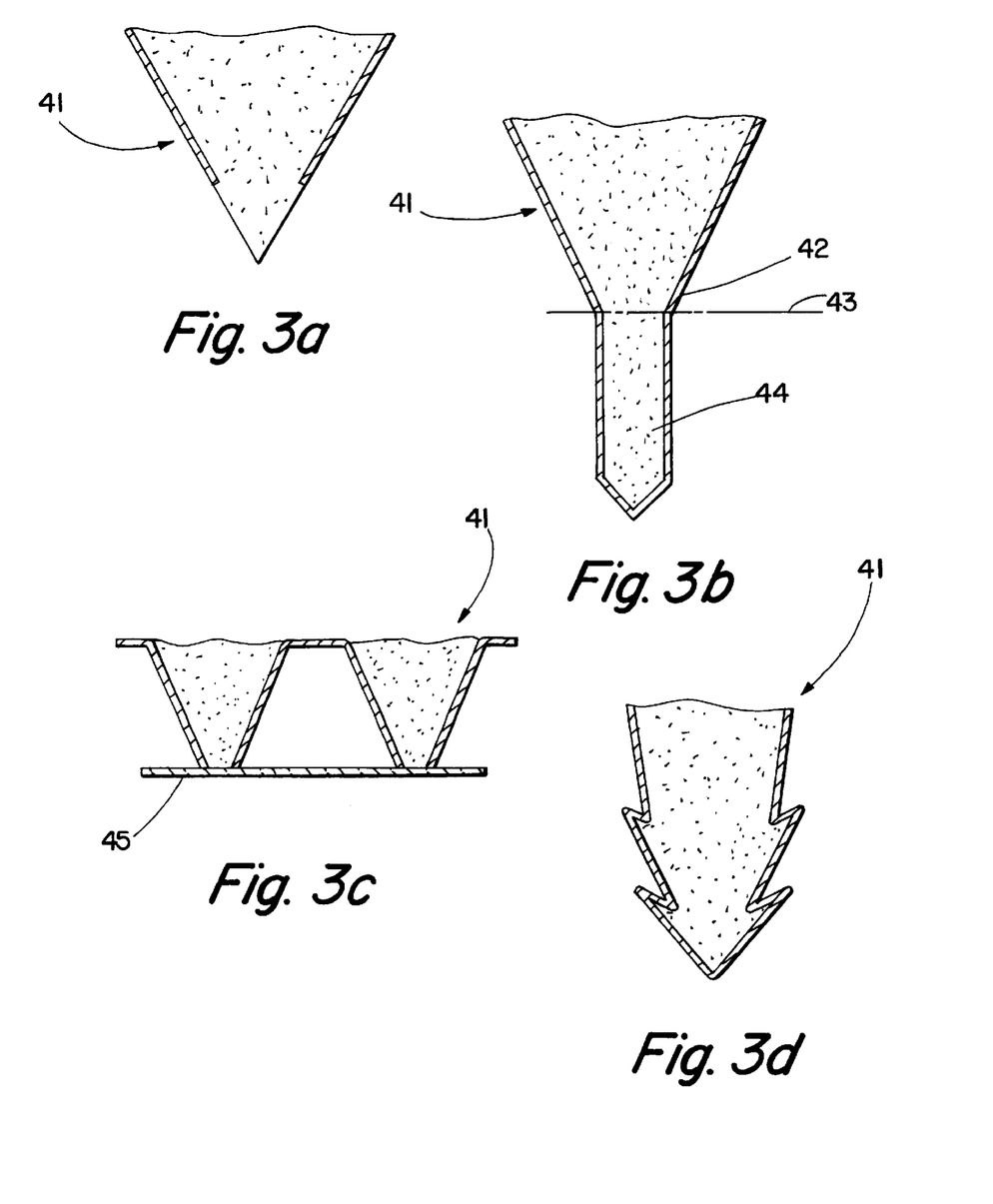
FIG. 3a–d show different shapes of micropins.

Embodiments of pins (41) are shown in FIG. 3. FIG. 3a shows a pin (41) which is porous at the tip and is therefore made permeable for the solution of active substance. FIG. 3b shows a pin (42) with a totally sealed outer wall. The tip has an extension (44) which breaks off at its root, the frangible point (43), when stuck in and thereby opens the previously sealed tip of the pin at the frangible point. Another possible method of opening the tips of the pins consists in covering the pin tips with a sealing film (45) which is torn away so as to "tear open" the pin tips (FIG. 3c). In order to anchor the transcorneal system, barbs may be formed on the pins, see FIG. 3d. The pins are basically made of a biologically acceptable material, e.g. a metal, ceramic or polymer, e.g. biodegradable polymers based on glycolide and/or lactide, preferably as a copolymer with other biodegradable polymers. The pins may be made from a porous material which is permeable to the active substance, e.g. a thermoplastic plastics material so that the active substance is released over the entire area of the pins.

Figure 4A:
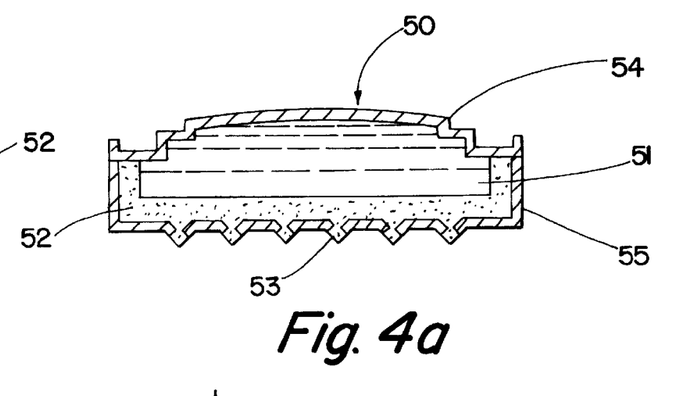
FIG. 4a shows a cross-sectional view of a transcorneal therapeutic system having a reservoir with a flexible membrane, before use.
Figure 4B:
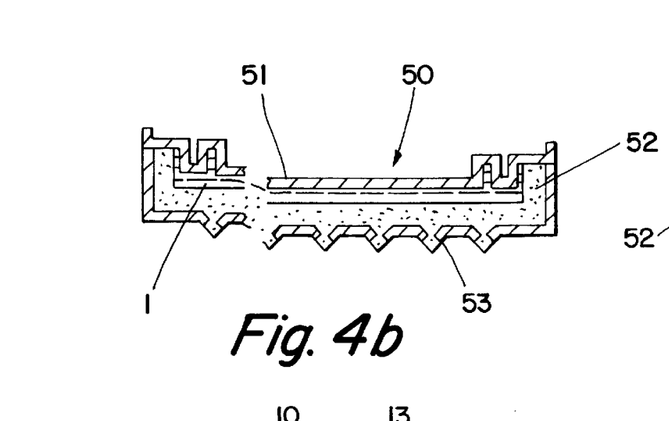
FIG. 4b shows a cross-sectional view of a transcorneal therapeutical system having a reservoir with a flexible membrane, after use.

FIG. 4 shows a tank-shaped reservoir (50) in which the solution of active substance (51) is sealed off from the outside by means of an elastic membrane (54). Depending on the embodiment of the transcorneal system according to the invention, the reservoir and the micro-pins (53) penetrating into the skin form a constructional unit. The reservoir wall (55) and the pins (53) are made of a porous material, as described above, the outer surface of which is sealed. The solution of active substance is injected into the active substance matrix (52) under slight overpressure. The overpressure is held by the elastic membrane (54) and thus helps to maintain a constant throughflow rate. The throughflow can also be briefly increased from the outside (by the patient) by pressing the membrane in order to achieve an additional dose. FIG. 4a shows the system according to the invention in its initial state; the outwardly convex membrane (54) ensures that the solution of active substance is under pressure and it is forced into the reservoir of active substance (52). The active substance passes through the micro-pins (53) and through the transcorneal layer of the skin in order to achieve a systemic activity. FIG. 4b shows the membrane (54) after the majority of the active substance solution has been used up.

Figure 5:
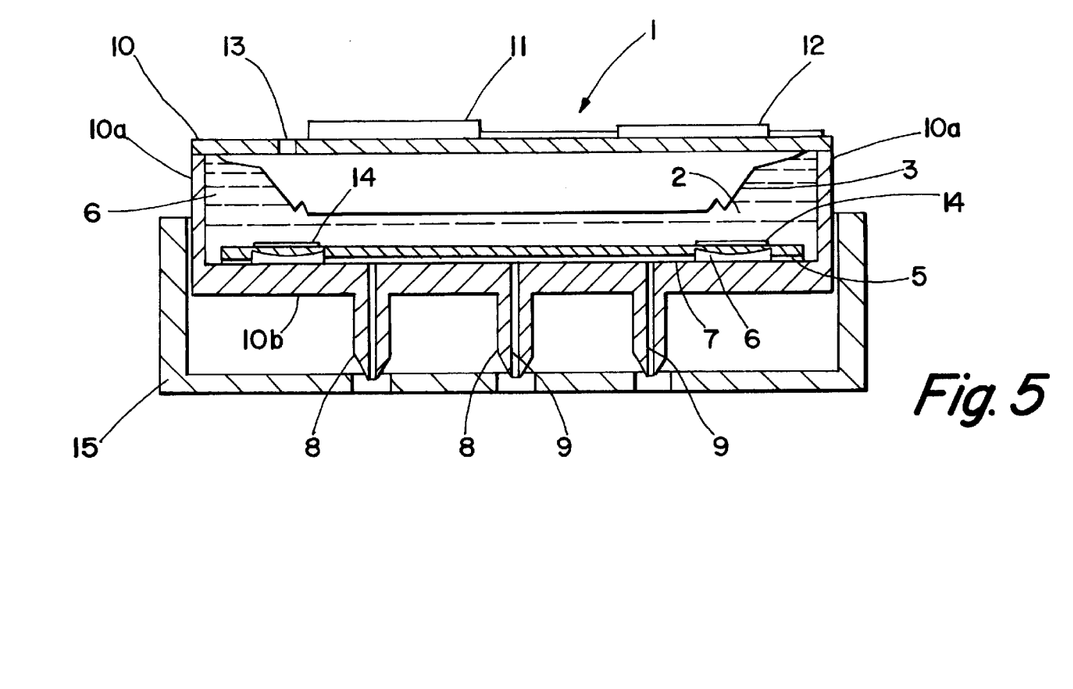
FIG. 5 shows a cross-sectional view of a transcorneal therapeutic system having a piezoelectric membrane to actively pump drug-containing fluid from the reservoir through the micropins and to the skin.

FIG. 5 shows a section through a transcorneal system (1). The housing (10) contains an active substance reservoir (2) which is sealed off at the top by a concertina (3). In the active substance reservoir is the active substance solution (4) which passes, at the bottom of the active substance reservoir, through an inlet channel (5) into a pump chamber (6). The solution runs through an outlet channel (7) to the micro-pins (8) arranged on the underside of the housing and from there through the capillary openings (9) of the micro-pins and out. The side parts (10a) of the housing and the underside (10b) of the housing together with the micropins form a structural unit, preferably of a thermoplastic plastics material. The lid of the housing contains the energy supply in the form of a battery (11) as well as electronic controls (12), whilst a ventilator (13) enables the concertina to adapt to the reduced volume as the solution of active substance is delivered through the micro-pins. The active substance solution is conveyed by means of a piezoelectric membrane (14), which performs an electrically controlled pumping movement. The inlet channel (5) is constructed so that the solution of active substance is pumped by the piezoelectric member (14) to the outlets of the micropins. This is done either by means of a valve or by the fact that the cross-section of the inlet channel is smaller than that of the outlet channel (7). Before the transcorneal system is used, the micro-pins are protected by a pin protector (15), e.g. in the form of a cap.

FIG. 6 shows some embodiments of the micro-pins according to the invention, in section and in plan view.

Figure 6A:
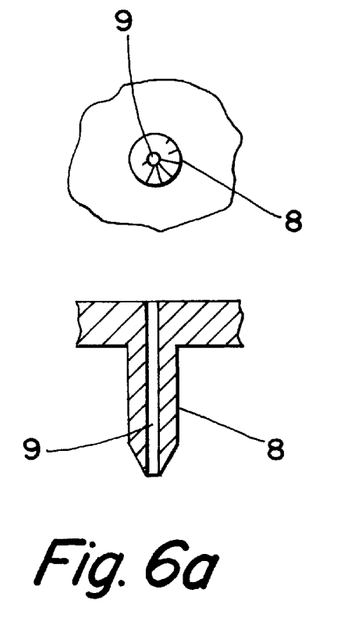
FIG. 6a–d show a cross-sectional view of micropins with capillaries or slots.

FIG. 6a shows a micro-pin having a central opening (9) and cylindrical outer shape (8) and a conical tip (10).

Figure 6B:
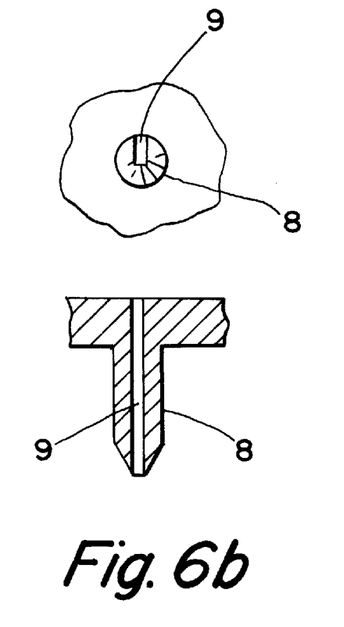

FIG. 6b shows a micro-pin having an opening in the form of a slot (9) and a cylindrical outer shape (8).

Figure 6C:
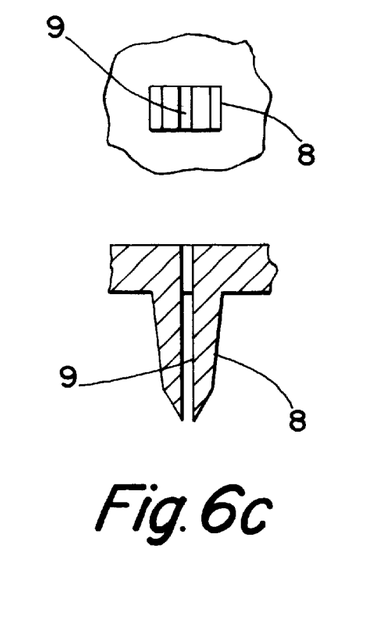

FIG. 6c shows a micro-pin with flattened outer sides (8), the opening being provided in the form of a slot.

Figure 6D:
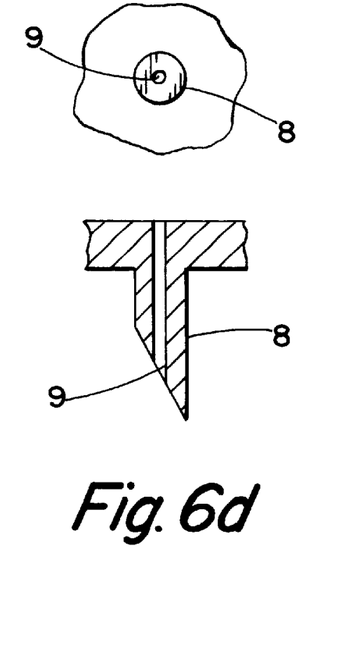

FIG. 6d shows a micro-pin with cylindrical outer shape and an inclined tip (10).

Figure 6E:
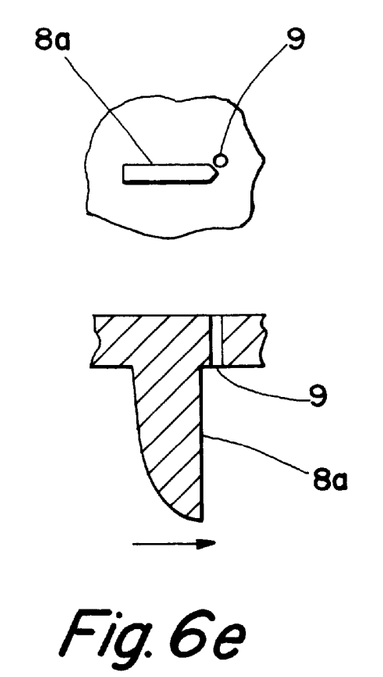
FIG. 6e–f show a cross-sectional view of micro-blades.

FIG. 6e shows an embodiment of the micro-blades according to the invention, which may be used instead of the micro-pins, in section and in plan view.

The openings (9) for the solution of active substance are usually close to the blade (8a) on the under side (10b) of the reservoir (see FIG. 5), so that the solution of active substance passes from there through the scratched surface of the skin and is able to develop its systemic activity.

Figure 6F:
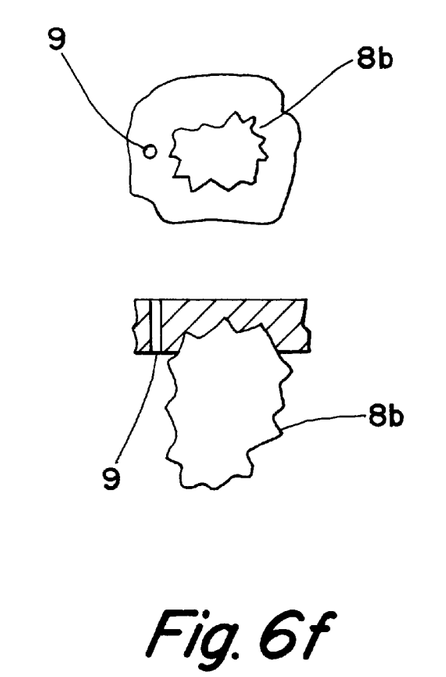

FIG. 6f shows an embodiment of a micro-blade in the form of a grain with short edges (8b) which scratch the skin. The opening or openings (9) is or are close to the grain.

The dimensions of the micro-blades are of approximately the same order of magnitude as the micro-pins described hereinbefore.

The individual micro-pins or micro-blades are typically arranged on the underside of the transcorneal system and form a structural unit; they may number between 10 and 100, for example.

The metering of the drug may be controlled by means of the flow volumes, which in turn depend on the total of the cross-sections of the openings in the micro-pins.

We claim:

1. A transcorneal system for controlled transcorneal delivery of a medicament into a warm-blooded animal comprising:

a) an active substance reservoir comprising a drug -containing liquid ;

b) a device, which device is provided with micro-blades which are capable of penetrating the stratum corneum of the animal and which device is also provided with a liquid-conveying means, whereby the device is connected to the reservoir via its liquid-conveying means to allow drug-containing liquid to pass from the reservoir to the micro-blades; and c) a means for actively controlling the passing of drug-containing liquid from the reservoir to the micro-blades, wherein the means for actively controlling the passing of drug-containing liquid from the reservoir to the micro-blades is an integrated pump with integrated electronic controls.

2. A transcorneal system for controlled transcorneal delivery of a medicament into a warm-blooded animal comprising:

a) an active substance reservoir comprising a drug-containing liquid;

b) a device, which device is provided with a plurality of micro-pins which are capable of penetrating the stratum corneum and which micro-pins have capillary openings at both ends and hollow spaces within the micro-pins and which device is connected to the reservoir via the capillary opening at one end of each of the micro-pins and is adjacent the stratum corneum at the opposite end of each of the micro-pins; and c) a means for actively discharging the drug-containing liquid from the reservoir through the micro-pins, wherein the means for actively discharging the drug-containing liquid is an integrated pump with integrated electronic controls.

3. The transcorneal system as recited in claim 2, further comprising microvalves between the reservoir and the capillary openings of the micro-pins.

4. The transcorneal system as recited in claim 2, wherein each micro-pins is provided with capillary openings that have a round cross-section.

5. The transcorneal system as recited in claim 2, wherein each micro-pin is provided with capillary openings that are slit-like.

6. The transcorneal system as recited in claim 2, wherein each micro-pin is made of a micro-porous material that is previous to the drug-containing liquid in the reservoir.

7. The transcorneal system as recited in claim 1, wherein the integrated pump is an electrically driven piezo-electric membrane performing a pump movement.

8. The transcorneal system as recited in claim 2, wherein the integrated pump is an electrically driven piezo-electric membrane performing a pump movement.

9. The transcorneal system as recited in claim 1, wherein the reservoir has at least one movable or flexible boundary surface.

10. The transcorneal system as recited in claim 2, wherein the reservoir has at least one movable or flexible boundary surface.

11. The transcorneal system as recited in claim 9, wherein the moveable boundary surface is a piston within a cylinder.

12. The transcorneal system as recited in claim 10, wherein the moveable boundary surface is a piston within a cylinder.

13. The transcorneal system as recited in claim 9, wherein the flexible boundary surface is a membrane.

14. The transcorneal system as recited in claim 10, wherein the flexible boundary surface is a membrane.

15. The transcorneal system as recited in claim 9, wherein the flexible boundary surface is a concertina.

16. The transcorneal system as recited in claim 10, wherein the flexible boundary surface is a concertina.

17. The transcorneal system as recited in claim 1, wherein the micro-blades have a length of at least about 10 $\mu$m.

18. The transcorneal system as recited in claim 1, wherein the micro-pins have a length of at least about 10 $\mu$m.

19. The transcorneal system as recited in claim 1, wherein the micro-blades are made of a thermoplastic material.

20. The transcorneal system as recited in claim 2, wherein the micro-pins are made of a thermoplastic material.

21. The transcorneal system as recited in claim 2, wherein each micro-pin has a tip with a radius of curvature of less than about 10 $\mu$m.

* * * * *